(12) United States Patent
Chung et al.

(10) Patent No.: US 7,438,719 B2
(45) Date of Patent: Oct. 21, 2008

(54) PHOTOTHERAPY SYSTEM AND DEVICE

(75) Inventors: Dong-Chune Christopher Chung, Dublin, CA (US); Abraham Totah, San Carlos, CA (US); Bryan Flaherty, Half Moon Bay, CA (US)

(73) Assignee: Natus Medical Incorporated, San Carlos, CA (US)

( * ) Notice: Subject to any disclaimer, the term of this patent is extended or adjusted under 35 U.S.C. 154(b) by 745 days.

(21) Appl. No.: 10/651,906

(22) Filed: Aug. 29, 2003

(65) Prior Publication Data

US 2005/0149149 A1 Jul. 7, 2005

Related U.S. Application Data

(63) Continuation-in-part of application No. 10/265,970, filed on Oct. 7, 2002, now Pat. No. 7,131,990.

(51) Int. Cl.
*A61N 5/06* (2006.01)
(52) U.S. Cl. .......................................... 607/88; 128/898
(58) Field of Classification Search ................. 128/898; 607/88–94
See application file for complete search history.

(56) References Cited

U.S. PATENT DOCUMENTS

| | | | |
|---|---|---|---|
| 4,907,132 A | | 3/1990 | Parker |
| 5,136,153 A * | | 8/1992 | Komiya et al. ........ 250/214 VT |
| 5,299,109 A | | 3/1994 | Grondal |
| 5,713,661 A | | 2/1998 | White |
| 5,800,479 A * | | 9/1998 | Thiberg ....................... 607/88 |
| 5,938,657 A | | 8/1999 | Assa et al. |
| 6,045,575 A | | 4/2000 | Rosen et al. |
| 6,166,496 A * | | 12/2000 | Lys et al. .................... 315/316 |
| 6,238,424 B1 * | | 5/2001 | Thiberg ....................... 607/88 |
| 6,290,713 B1 | | 9/2001 | Russell |
| 6,325,793 B1 | | 12/2001 | Tomita |
| 6,379,022 B1 * | | 4/2002 | Amerson et al. ............ 362/231 |
| 6,414,801 B1 | | 7/2002 | Roller |
| 6,464,714 B1 | | 10/2002 | Mewissen et al. |
| 6,554,439 B1 * | | 4/2003 | Teicher et al. .................. 362/2 |
| 6,596,016 B1 | | 7/2003 | Vreman et al. |
| 6,676,655 B2 * | | 1/2004 | McDaniel ....................... 606/9 |
| 6,921,182 B2 * | | 7/2005 | Anderson et al. ........... 362/231 |
| 6,936,044 B2 * | | 8/2005 | McDaniel ....................... 606/9 |
| 7,001,413 B2 * | | 2/2006 | Butler ........................ 607/88 |
| 7,081,128 B2 * | | 7/2006 | Hart et al. ..................... 607/89 |
| 7,088,321 B1 * | | 8/2006 | Parker ......................... 345/83 |

(Continued)

OTHER PUBLICATIONS

Hendrik J. Vreman et al., "Light Emitting Diodes: A Novel Light Source for Phototherapy," Pediatric Research, Nov. 1998, pp. 804-809, vol. 44, No. 5.

*Primary Examiner*—Henry M Johnson, III
(74) *Attorney, Agent, or Firm*—Temmerman Law Office; Matthew J. Temmerman; Daniel Maguire

(57) ABSTRACT

A phototherapy system and device is disclosed, including an array of light sources from at least two distinct spectral light regions. The first spectral light region represents the treatment color, and thus is chosen for its phototherapeutic value. For instance, blue light may be the treatment color for hyperbilirubinemia. The second spectral light region represents the balancing color, and is chosen for its ability to mitigate discomfort that may be caused by viewing the treatment color. When blue is the treatment color, yellow has been found to be an effective balancing color.

5 Claims, 6 Drawing Sheets

U.S. PATENT DOCUMENTS

| | | | |
|---|---|---|---|
| 2002/0198575 A1* | 12/2002 | Sullivan | 607/88 |
| 2003/0233138 A1* | 12/2003 | Spooner | 607/93 |
| 2004/0022050 A1 | 2/2004 | Yamashita et al. | |
| 2006/0293727 A1* | 12/2006 | Spooner et al. | 607/88 |

* cited by examiner

PHOTOTHERAPY SYSTEM AND DEVICE

RELATED APPLICATIONS

This application is a continuation-in-part of and claims priority from application Ser. No. 10/265,970 (filed Oct. 7, 2002), granted as U.S. Pat. No. 7,131,990 on Nov. 7, 2006, and itself claiming priority from provisional application 10/651,906 filed Aug. 29, 2003 and now abandoned. The disclosure of application Ser. No. 10/265,970 is incorporated herein as if set out in full.

BACKGROUND OF THE INVENTION

1. Field of the Invention

This invention relates to devices and methods for the phototherapeutic treatment of illness and diseases.

2. General Background

Phototherapy is a promising clinical tool for the treatment for many conditions, including seasonal affective disorder, bulimia nervosa, herpes, psoriasis, sleep disorders, acne, and skin cancer.

Phototherapy is especially promising as a treatment for hyperbilirubinemia, a common condition affecting 60-70% of all full-term infants. Hyperbilirubinemia is caused by the accumulation of excess bilirubin in the blood and skin of the infant. This excess bilirubin turns the skin and sclera a characteristic yellow color. If left untreated, extreme cases of hyperbilirubinemia can result in neurological insult (kernicterus) or even death. A common treatment for hyperbilirubinemia is phototherapy, in which the infant is exposed to light in a range corresponding to the peak absorption spectra for bilirubin (blue-green, 400-520 nm). This light changes the form of the bilirubin to a different isomer that is more readily eliminated by the body.

A number of different light sources can be used for phototherapy. Traditionally, broadband sources have been used, such as fluorescent, halogen, or incandescent light. However, it has been recently suggested that light emitting diodes (LEDs) can be an effective phototherapeutic light source.

Blue LEDs have been effectively used to treat hyperbilirubinemia, but some individuals report a feeling of nausea or discomfort from prolonged exposure to blue light. Thus, there is a need for a method of relieving the discomfort these individuals feel, without compromising the effectiveness of the phototherapy.

SUMMARY OF THE INVENTION

The present invention is a phototherapy system with light sources covering at least two distinct spectral light regions. The spectral light region of the first set of light sources is chosen for its phototherapeutic value. This spectral light region, which need not be a continuous part of the spectrum, will be referred to as the "treatment color." The spectral light region of the second set of light sources is chosen for its ability to mitigate any nausea or other discomfort from viewing the treatment color. This spectral light region will be referred to as the "balancing color." In one embodiment, the treatment color is blue, and the balancing color is yellow. This embodiment can be used to be treat hyperbilirubinemia.

DETAILED DESCRIPTION

The present invention is a phototherapy system and device, including (i) an optional stand 10, (ii) an enclosure 30, and (iii) an array of light sources 40 in the enclosure 30. The array includes treatment color light sources (such as blue) and balancing color light sources (such as yellow).

Figure 1:
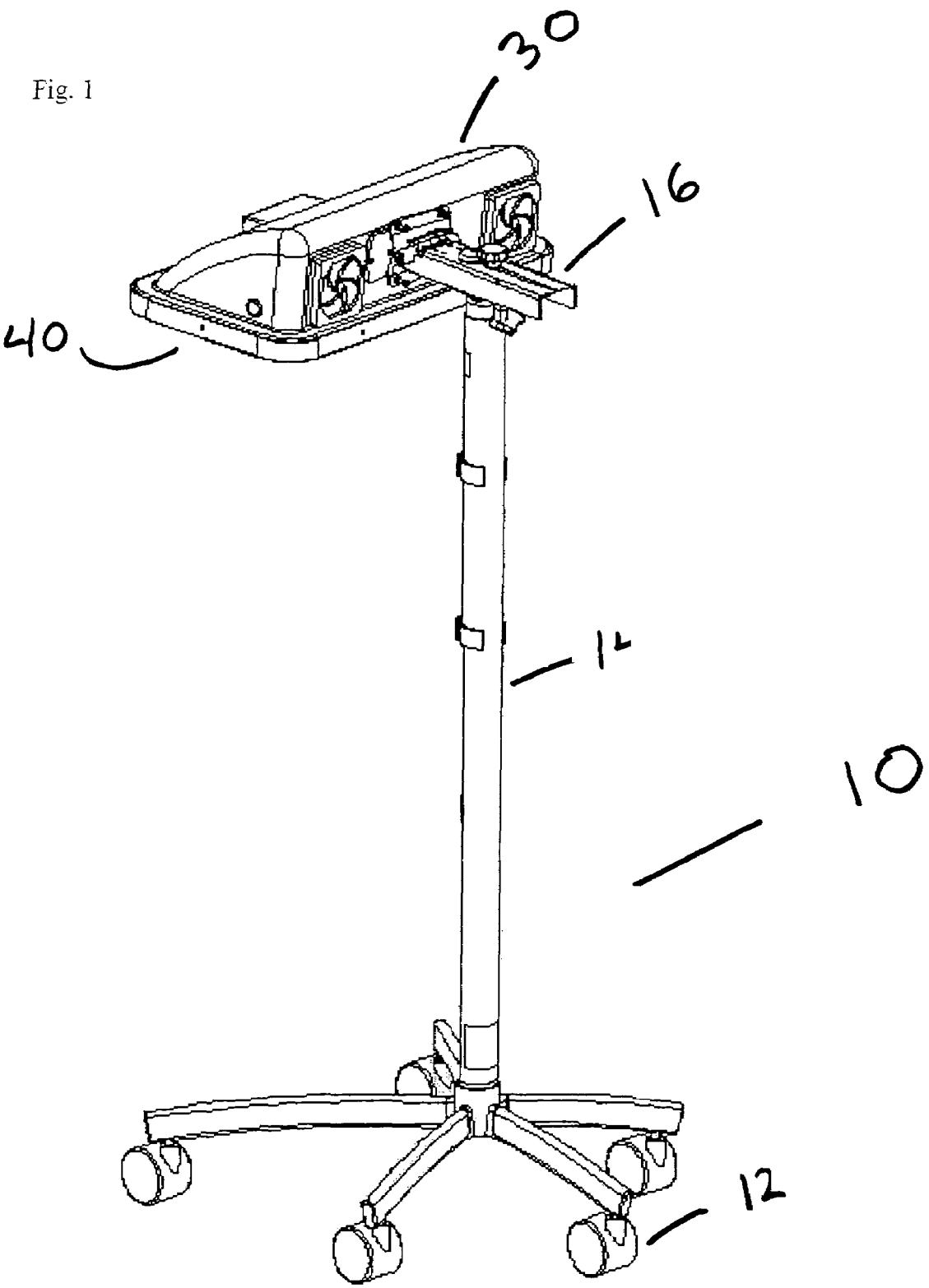
FIG. 1. is a perspective view of a device according to the present invention, with a stand.
Figure 7:
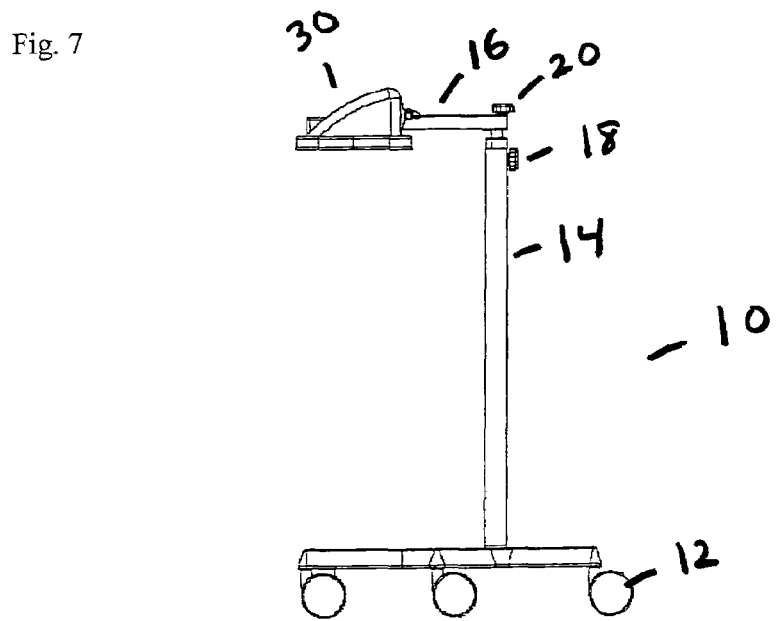
FIG. 7 is a side view of a device according to the present invention, with a stand.

As depicted in FIGS. 1 and 7, the optional stand 10 is used to hold the light sources over the subject. The stand 10 may have wheels 12, a vertical extension 14, and a horizontal extension 16. It may also have height control means 18 to raise or lower the enclosure 30, and horizontal positioning means 20 to control the horizontal position of the enclosure 30. The stand is optional, and other means can be used to hold the array of lights over the subject. For instance, the array can be clipped or fastened over a bassinet, incubator or bed. Depending on the light source used, the array 40 can be distant or very close to the subject.

Figure 2:
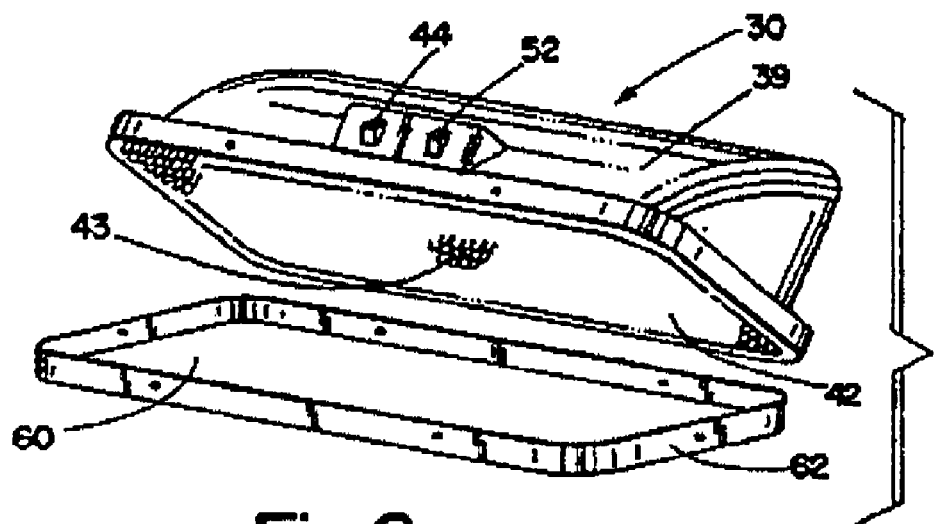
FIG. 2. is a perspective view of a device according to the present invention, without a stand, and with the enclosure tilted up to reveal exemplary LED light sources.
Figure 3:
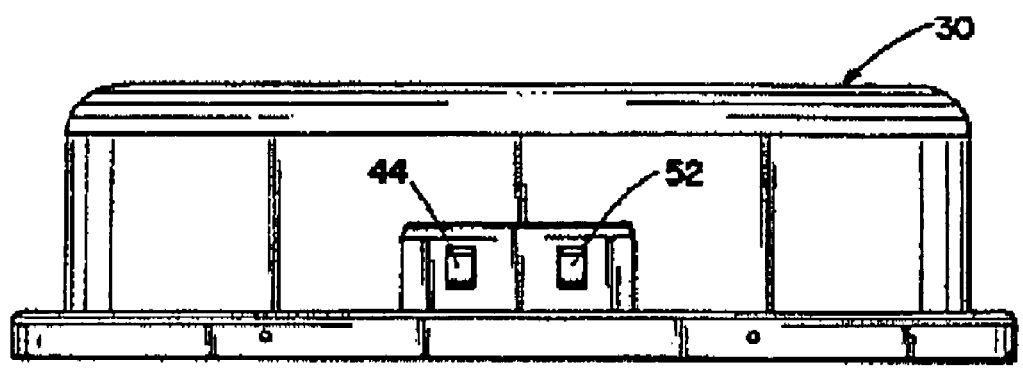
FIG. 3 is a front view of a device according to the present invention, without a stand.
Figure 4:
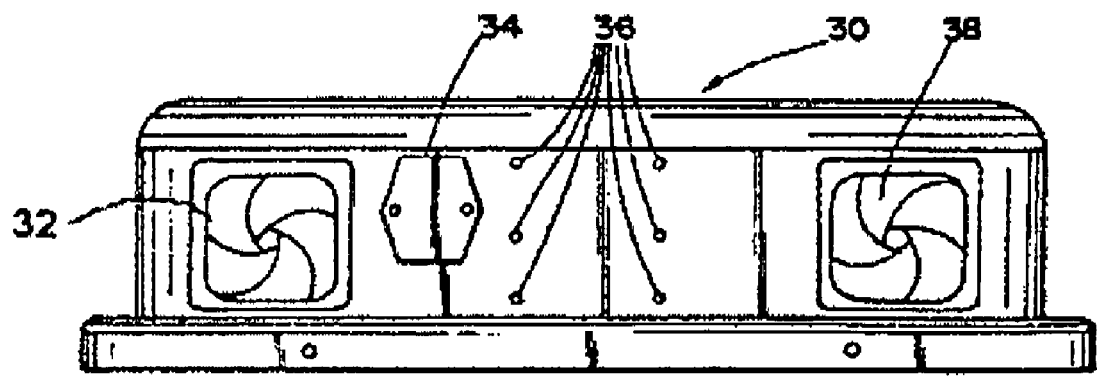
FIG. 4 is a back view of a device according to the present invention, without a stand.
Figure 5:
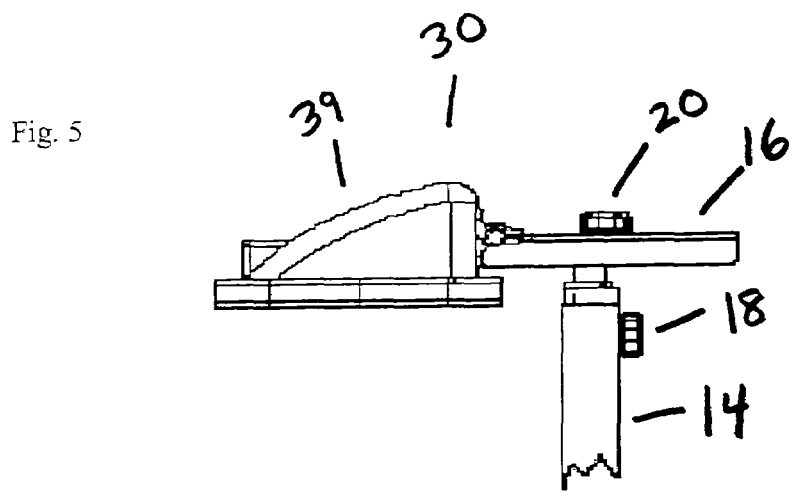
FIG. 5. is a side view of a device according to the present invention, without a stand.
Figure 6:
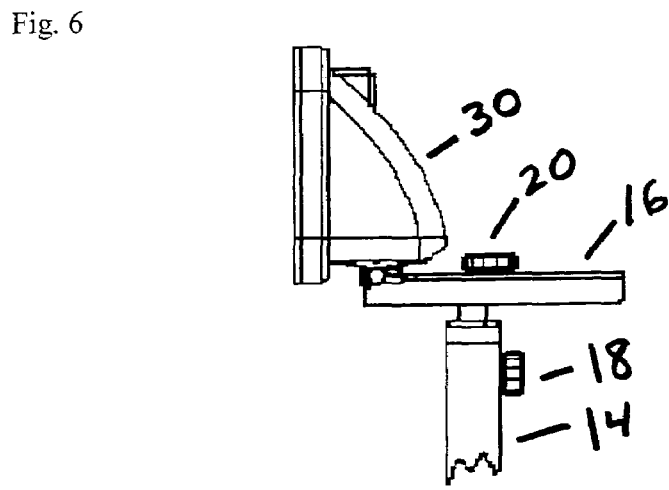
FIG. 6 is a side view of a device according to the present invention, without a stand, and with the enclosure tilted up.

The enclosure 30 can be mounted on the stand so that it can be easily tilted. (See FIG. 6). The enclosure 30 simply provides structural support for the sockets or board which hold the array of light sources 40. For instance, FIG. 2 shows the enclosure 30 with an LED board 42. The precise form of the enclosure is irrelevant to the present invention. Indeed, for purposes of this patent, "enclosure" is defined to mean any structure that holds the light sources. As shown in FIGS. 2 & 4, at the back of the enclosure there is an exhaust 32, a power entry module 34, attachment plate 36 to attach the enclosure to the stand 10, an air inlet 38, and a top surface 39. The top surface 39 may angled to discourage the placement of spillable liquids on the top of the device.

The enclosure can be made of many materials, including but not limited to metal or various kinds of plastic or polyvinyl materials. Typically, the enclosure will be a rigid structure. However, it is possible to use a flexible enclosure to be used in embodiments in which the enclosure is wrapped around the subject.

The array of light sources 40 is a plurality of band-limited light sources, such as semiconductor light sources, LEDs 42, halogen lights, low-intensity lasers, etc. The array can take a number of different forms, and the distribution of lights in the array can be uniform or nonuniform.

Switches are used to control the light sources, and in one embodiment, a switch 44 can provide for operation in either a high or low intensity mode. Alternatively, a potentiometer could be added to provide more precise control or to provide a wider range of light intensity. Also, diffusers and other optical intensity adjustment devices can be used to adjust the intensity of the light. For purposes of this patent, an "optical intensity adjustment device" is any device that can alter the intensity of emitted light.

Figure 8A:
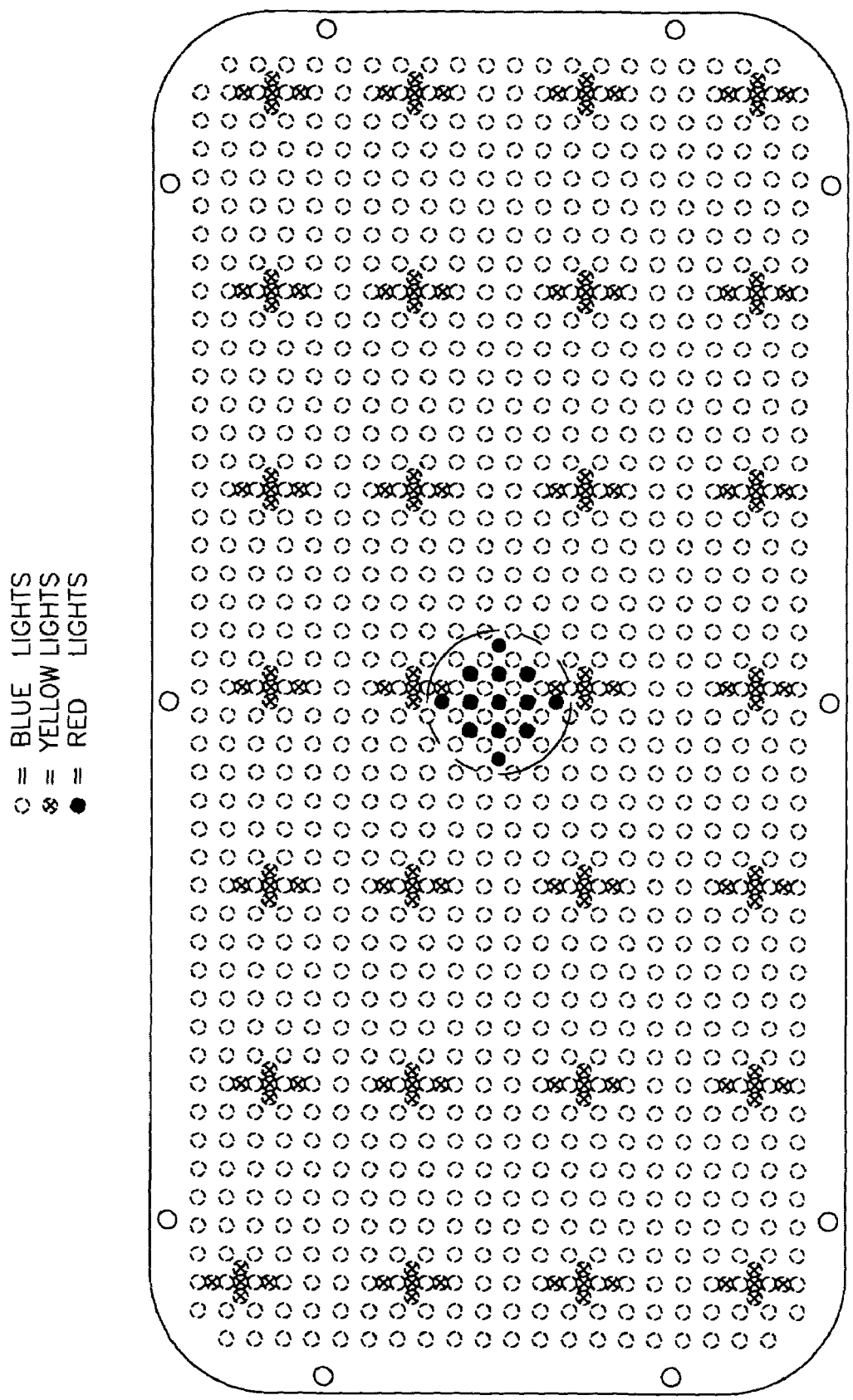
FIGS. 8a and 8b are schematic depictions of exemplary phototherapy arrays according to embodiments of the present invention.
Figure 8B:
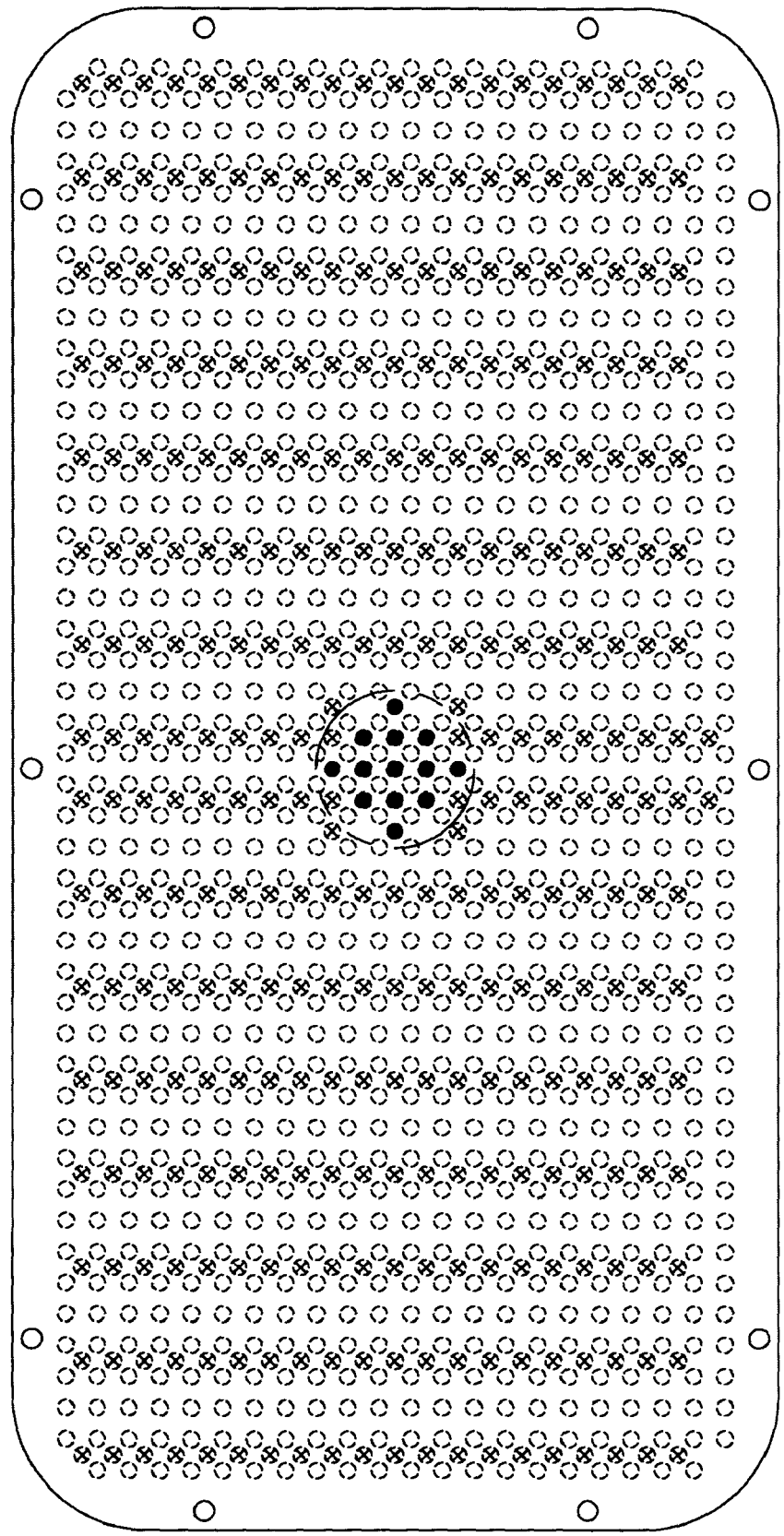

The array includes light sources covering at least two different spectral light regions. See FIG. 8. The first spectral light region—the treatment color—is chosen for its photo-therapeutic value. Thus, in one embodiment, the treatment color can be blue, for use in treating hyperbilirubinemia. Other exemplary treatment colors include red for treatment of psoriasis.

The second spectral light region—the balancing color—is chosen for its ability to modify perception of the treatment color and thereby mitigate the nausea or other negative effects that result from viewing the treatment color. For instance, some healthcare workers have reported nausea from exposure to blue light LEDs. It has been found through trial and error that interspersing yellow LEDs into an array of blue LEDs mitigates or eliminates that effect. Yellow light seems to relieve blue light nausea better than other colors. For purposes of this patent, "blue" light is in the range of 400 nm to 520 nm, and "yellow" light is in the range of 547 nm to 619 nm. Green, red, or orange light sources can also be used for the balancing color when blue light is used for the treatment light.

Figure 9:
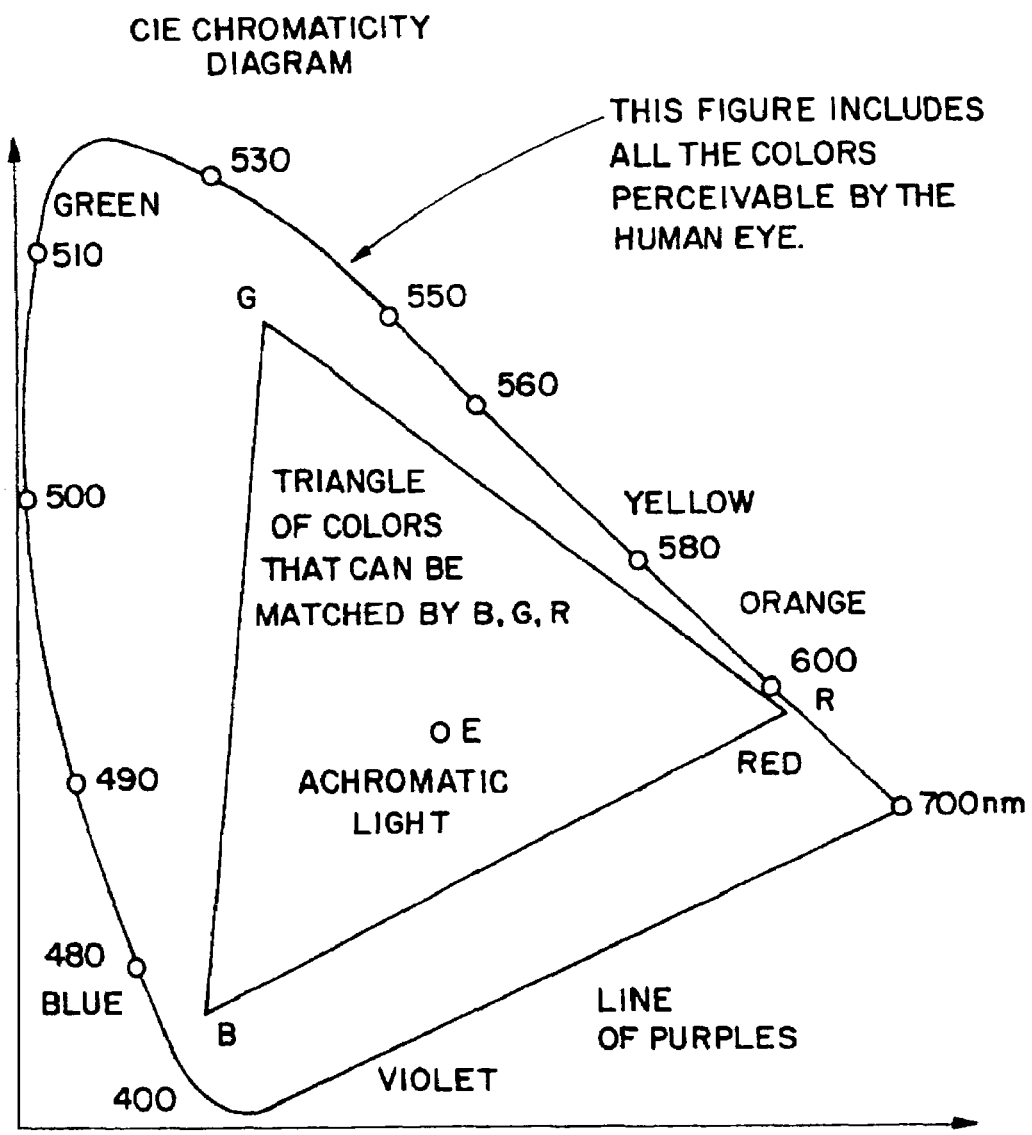
FIG. 9 is a chromaticity table.

For other phototherapeutic colors, the balancing color can be determined by experimentation to gauge what color most effectively relieves the symptoms caused by the treatment color. The balancing color may be the spectral light range that produces a perception of white or non-treatment color when combined with the treatment color. A chromaticity table, such as the one provided as FIG. 9, can be used to find the appropriate balancing color, by drawing a line from the treatment color through the central point indicating white light, and then determining where the line intersects the color line.

Multiple balancing colors can be also used. Thus, for instance, red and yellow light can be used to balance the blue light used to treat hyperbilirubinemia. Additionally, the intensity of the balancing color or colors can be adjusted to achieve the desired effect.

In order to adequately modify the phototherapeutic color, a sufficient amount of balancing color light is required. In one embodiment, a ratio of about 3 blue LEDs to 1 yellow LEDs of equal intensity has been found sufficient. Of course, the appropriate ratio will depend on a number of factors, including the intensity of both the treatment LEDs and the balancing LEDs, and on the color perception that is sought.

The balancing color light sources can be arranged in the array in a number of ways, including random distribution, various uniform distributions, distribution about the periphery of the array, and even placement in a separate array or enclosure. Exemplary arrays are provided in FIGS. 8a and 8b. In these figures, a target light of red LEDs is also shown.

The present invention can be practiced with many different types of narrow-band or limited spectral range light sources, including semiconductor light sources, LEDs and low-intensity lasers. For purposes of this patent, the term "limited spectral range light source" will be used to generically refer to any light source that emits light from any spectral range except the range that includes all visible colors, i.e. white light. In one embodiment, approximately 1000 blue-green (420-500 nm) LEDs can be used to treat hyperbilirubinemia, along with 320 yellow LEDs. Such LEDs are commercially available from CREE, Inc. (4600 Silicon Drive, Durham, N.C. 27703) and Nichia America Corporation (3775 Hempland Road, Mountville, Pa. 17554). The number of light sources in the array will vary based on their intensity and on the nature of the phototherapeutic treatment.

Typically, the light sources 40 would shine down on the subject. However, they can also be oriented upwards, and bounce off an optional reflector on the enclosure. Such a reflector can be curved into a convex formation, to diffuse the light away from the center of the subject, or to otherwise alter the intensity, distribution, or light properties of the array.

Also, the light sources can be arranged to shine from the side, such as through a transparent bassinet, or from the bottom, or any combination thereof.

Both the treatment color light sources and the balancing color light sources may be illuminated continuously or discontinuously, and the present invention is not limited by the duration, frequency, or pattern of illumination for either or both set of light sources. Thus, the lights may illuminated synchronously, asynchronously, in a staggered manner, in a random manner, or in accordance with a predefined frequency or duty cycle (ratio of illuminated time to non-illuminated time). In one embodiment, a duty cycle of below 0.5 is used.

In operation, the subject may be placed under the phototherapy device, and both the treatment color and balancing color light sources may be illuminated simultaneously. The subject will then receive phototherapy, and the healthcare workers administering the treatment may not feel the nausea that sometimes results from exposure to a single color light such as blue. The balancing color changes the perception of the health care workers so that instead of perceiving only the treatment color, the workers perceive a blended, balanced, or alternative color. The intensity of the balancing color can be adjusted as necessary to achieve the desired balanced or altered perception.

One skilled in the art will appreciate that the present invention can be practiced through a number of embodiments, including but not limited to those specifically described in this patent. Therefore, the embodiments, dimensions, and materials described in this patent are presented for illustration, not to limit the scope of the claims.

We claim:

1. A method of modifying a health care worker's perception of a plurality of limited spectral range treatment color light sources, comprising:
   causing a subject to receive light from a first plurality of limited spectral range balancing color light sources having a wavelength of between 547 nm and 619 nm while said subject is receiving light from treatment color light sources having a wavelength of between 400 nm and 520 nm, wherein at least one individual has a perception of a blended color, said perception comprising said treatment color light sources and said balancing color light sources, and wherein the ratio of said treatment light sources to said balancing color light sources is between approximately 3:1 and approximately 7:1.

2. The method according to claim 1, wherein the ratio of said treatment light sources to said balancing color light sources is approximately 3:1.

3. A phototherapy system, comprising:
   a limited spectral range treatment light source emitting light having a wavelength of between 400 nm and 520 nm;
   a first limited spectral range balancing light source emitting light having a wavelength of between 547 nm and 619 nm;
   wherein the ratio of intensity of said treatment light source to said balancing light source is between approximately 3:1 and approximately 7:1; and
   wherein there are a plurality of said treatment light sources and said balancing light sources, and wherein the ratio of said treatment light sources to said balancing light sources is approximately 3:1.

4. An array of phototherapeutic lights sources, comprising limited spectral range lights of a treatment color having a wavelength of between 400 nm and 520 nm and limited spectral range lights of a balancing color having a wavelength of between 547 nm and 619 nm, wherein said balancing color is chosen for its ability to mitigate the health or comfort effects on humans from viewing said treatment color; and wherein the ratio of said treatment light sources to said balancing light sources is approximately 3:1.

5. The array according to claim 4, wherein said treatment color is blue and said balancing color is yellow.

* * * * *